United States Patent [19]

Nilsson et al.

[11] Patent Number: 4,788,148

[45] Date of Patent: Nov. 29, 1988

[54] PLASMID WITH STABILIZED INHERITANCE

[75] Inventors: Lars A. J. Nilsson, Lund; Stig G. Skogman, Akarp, both of Sweden

[73] Assignee: A C Biotechnics AB, Arlöv, Sweden

[21] Appl. No.: 664,435

[22] Filed: Oct. 24, 1984

[30] Foreign Application Priority Data

Oct. 24, 1983 [SE] Sweden .................. 8305838-8

[51] Int. Cl.[4] .................. C12N 1/00; C12N 1/20; C12N 9/00; C12P 13/22
[52] U.S. Cl. .................. 435/320; 435/108; 435/183; 435/253; 935/14; 935/29; 935/38; 935/73
[58] Field of Search .................. 435/317, 172.3, 91, 435/108, 183, 253, 230; 935/56, 14, 38, 72, 73, 29

[56] References Cited

U.S. PATENT DOCUMENTS

| | | | |
|---|---|---|---|
| 4,237,224 | 12/1980 | Cohen et al. | 935/41 X |
| 4,371,614 | 2/1983 | Anderson et al. | 435/108 |
| 4,371,615 | 2/1983 | Miwa et al. | 935/73 X |
| 4,436,815 | 3/1984 | Hershberger et al. | 935/73 X |

OTHER PUBLICATIONS

Olson, N. J., Dissertation Abstracts International, vol. 44/02-B p. 415, Abstract #814174, Jun. 7, 1983.
Yamao et al., Journal of Biological Chemistry (1982) pp. 11639-11643.
R. W. Old, et al; Principles of Gene Manipulation, Studies in Microbiology vol. 2, pp. 23-24.
Marjorie A. Tingle, et al; Mapping of a Structural Gene . . . ; J. of Bacteriology, (5/1969), pp. 837-839.
Robert C. Bohinski; Modern Concepts in Biochemistry, Third Edition; pp. 597-598.
F. C. Neidhardt, et al; Phage-Induced Appearance of a Valyl sRNA . . . ; Cold Spring Harbor Symposia on Quantitative Biology, vol. 31, (1967), pp. 557-563.

Primary Examiner—Thomas G. Wiseman
Assistant Examiner—Charles L. Patterson, Jr.
Attorney, Agent, or Firm—Oblon, Fisher, Spivak, McClelland & Maier

[57] ABSTRACT

A plasmid with stabilized inheritance containing at least one production gene introduced colinearly by gene technology. The plasmid is characterized by a nucleic acid fragment colinearly introduced therein and constituted by the gene for valyl-tRNA synthetase; cell containing such plasmid; and a process for preparing the plasmid.

6 Claims, 2 Drawing Sheets

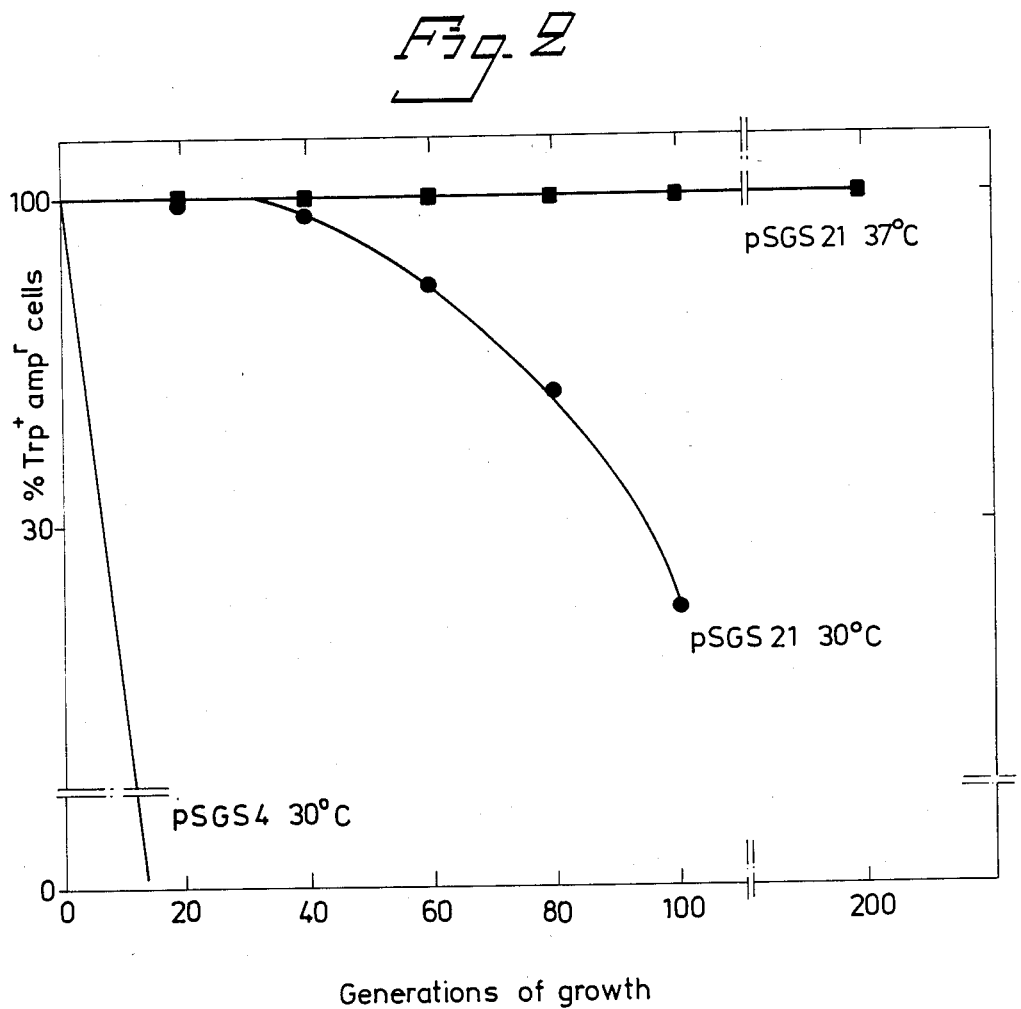

PLASMID WITH STABILIZED INHERITANCE

The present invention relates to plasmids with stabilized inheritance containing at least one production gene introduced colinearly by gene technology. The invention also covers host cells for such plasmids and process for the preparation of the plasmid.

During the last years there has been an increasing interest to use bacteria for the production of different compounds, such as interferones, insulin, different growth hormons and several aminoacids.

The common strategy for providing over production of the desired substance is to isolate from a natural source or by chemical syntheses the genes coding for the desired substance or for the enzymes in the biosynthetic pathway leading to the desired product. The isolated genes are then introduced on an extra chromosmal DNA molecule, a plasmid, which is present in the cell in varying amounts.

In order for an autonomously replicating plasmid to be propagated stably within a growing bacterial cell population, two requirements must be satisfied. First, the rate of replication of the plasmid must be monitored by some mechanism and adjusted to the growth rate of the culture. Second, stable maintenance of plasmids in growing cell populations also requires that both of the daughter cells produced during cell division receive at least one copy of each plasmid species present in the parent cell. The plasmid into which the desired gene is to be introduced is normally stably inherited, i.e. at least one plasmid molecule is distributed to each daughter cell at cell division. However, when "foreign" genes, i.e. genes normally not found on the plasmid, are inserted into the plasmid the stability of the plasmid will be subject to decrease and more and more cells free of plasmid appear in the growing cell population. Since such plasmid free cells no longer produce the desired product the yield will decrease to a level which is not practically feasible.

Up to now one has tried to overcome the disadvantage of unstable inheritance by introducing a gene that confers resistance to a certain antibiotic into the production plasmid. In this manner only cells which contain the plasmid are resistant to the antibiotic. By growing the cells in a medium containing the antibiotic selection for plasmid containing cells will be obtained in that cells which have lost the plasmid will die away.

The use of antibiotic in selection has, however, several disadvantages, among which the following may be mentioned:

(a) Introducing an antibiotic increases production costs;
(b) there is risk for antibiotic contamination in the final product and difficulties arise in purification of the product;
(c) the antibiotic has to be destroyed before discharge of waste water from the fermentation;
(d) there is risk for environmental distribution of antibiotic resistant genes.

The invention has for its purpose to provide for a plasmid with stabilized inheritance, the plasmid containing at least one production gene colinearly introduced into the plasmid.

Another object of the invention is to provide cells containing such plasmid.

Yet another object of the invention is to provide a process for the preparation of an autonomically replicating plasmid containing a desired production gene.

The present invention has made it possible to avoid the disadvantages associated with the technique of using antibiotics as outlined above, and in accordance with the invention the plasmid in addition to the desired production gene or genes carries the gene for the enzyme valyl-tRNA synthetase. It has been found that colinear introduction into the plasmid of this gene provides for stabilized inheritance, as will be shown further below.

To provide for production of the desired substance the plasmid carrying the valyl-tRNA synthetase gene, also called the valS gene, is introduced into a bacterial cell which lacks valyl-tRNA synthetase activity. This may be accomplished for example by mutating the host cell in the chromosomal valyl-tRNA synthetase. This chromosomal mutation has altered the enzyme in such a way that it shows no activity at an elevated temperature, i.e. at 37° C. or higher. This has for an effect that if the plasmid containing cells are grown at such elevated temperature plasmid free segregants are unable to grow and the plasmid containing the production gene is thus stably inherited.

Temperature sensitive mutants in the valyl-tRNA synthetase can be isolated by mutagenization with any mutagenizing agent. Cells unable to grow at an elevated temperature are screened and the valyl-tRNA synthetase activity is determined. Cells lacking in vitro activity in the valyl-tRNA synthetase are chosen for genetical analysis of the mutation, and mutants showing high cotransduction with pyrB are selected. From such mutants the temperature sensitive valS gene is introduced into the strain to be used.

The plasmid used in accordance with the invention is suitably derived from naturally occurring autogenerating genomes in procaroytic organisms. The production gene of the plasmid is preferably directed to the production of a primary metabolite. The production gene can be directed to the production of an amino acid, for example tryptophan.

The host cell containing the plasmid of the invention may suitably belong to the species *E. coli*, such as the strain GRB 238.

The invention also covers a process for the preparation of an autonomically replicating plasmid containing the desired production gene colinearly arranged therein. In this process there is introduced into the nucleic acid chain, in a manner known per se, a first nucleic acid fragment containing the production gene and a second nucleic acid fragment containing the gene for valyl-tRNA synthetase. In the process the nucleic acid chain is suitably opened by means of restriction enzymes, the subsequent plasmid syntheses being performed enzymatically. It is preferred first to introduce one nucleic acid fragment and then the other.

BRIEF DESCRIPTION OF THE DRAWINGS

FIG. 2 is a graph showing the stability of plasmid pSGS21 compared with pSGS4.

Figure 1:
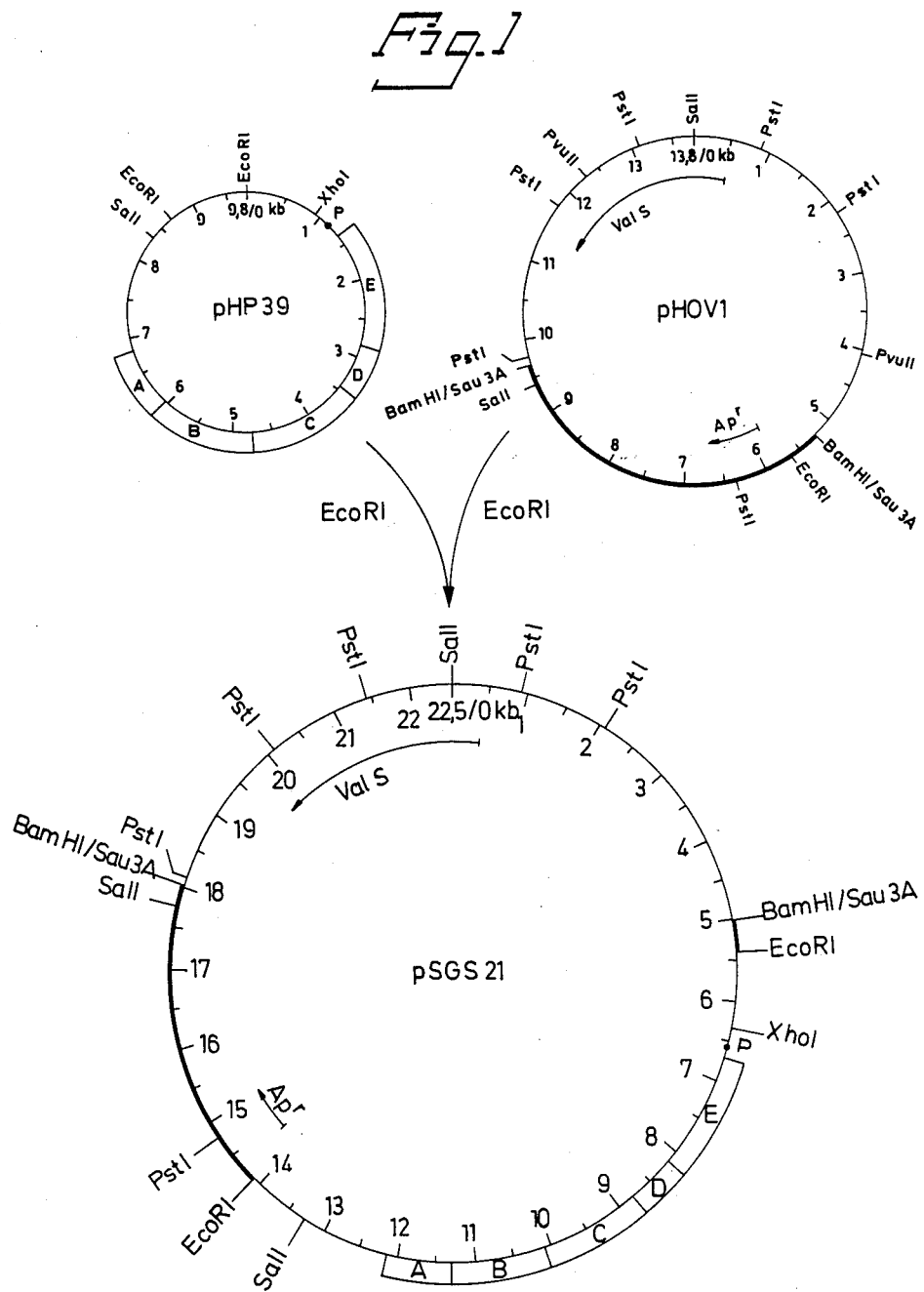
FIG. 1 shows the production of plasmid pSGS21, a stable valS-trp plasmid, from plasmid pHP39 containing the trp operon and plasmid pHOV1 containing the valS operon.

The invention will now be described by specific examples which, however, must not be construed as limiting the scope of the invention. For details regarding the stabilizing gene, valyl-tRNA synthetase, reference is had to Eidlic and Meidhardt (Ref. 8).

I. Isolation of a ColE1-hybrid carrying the gene for the valyl-tRNA synthetase (the valS gene)

Temperature resistant conjugants were isolated on LA plates from the Clarke and Carbon collection (Table 1) with strain GRB238 (Table 1) as a recipient. Several of the clones obtained were analysed for plasmid content by agarose-gel electrophoresis of miniclear lysates. One of the clones was shown to harbour a plasmid that after isolation transferred temperature resistant valS activity and showed a three fold increase in the specific valS activity compared to a wild type strain (Table 2).

II. Subcloning of the valS gene

One μg of plasmid DNA from the clone described under section I. was partially cleaved with restriction endonuclease Sau3A. This DNA was mixed with 1 μg pBR322 DNA, linearized with restriction endonuclease BamH1.

The DNA mixture was then ligated and transformed into competent cells of strain GRB238. Temperature resistant transformants were selected at 40° C. on LA-plates. One of the transformants carried a 9400 bp insert in the BamH1 site in pBR322 (see FIG. 1) coding for the valS gene. This plasmid, pHOV1 gave an 8 fold increase of the specific valS activity (see Table 2).

III. Construction of a valS-trp+ plasmid

1 μg of pHOV1 and pHP39 DNA, respectively, was digested with the restriction enzyme EcoR1 giving three fragments, one 13.8 kb which is the linearized pHOV1 plasmid, one 8.7 kb carrying the trp operon from pHP39 and one 1.1 kb fragment. The DNA mixture was ligated and competent GRB238 cells were transformed with the ligated DNA mixture and temperature resistant transformants were selected at 40° C. The latter were screened for trp+ phenotype. 10 of the clones obtained were analysed by agarose gel electrophoresis of mini clear lysates and were shown to carry equally large plasmids, about 22.5 kb in size. One of these plasmids pSGS21 (FIG. 1), was analysed by cleavage with restriction endonucleases. Digestion with EcoR1 gives two fragments, one 13.8 kb equal to linearized pHOV1 and one 8.7 kb equal to the trp carrying fragment from pHP39. The relative specific activity for the valyl-tRNA synthetase in strain GRB238 harbouring plasmid pSGS21 was 6 times that of the control. The slightly lowered value compared to GRB238 containing pHOV1 is probably due to a lower copy number for pSGS21 due to the increase in amount of DNA in the plasmid.

IV. Stability of the valS-trp plasmid

The stability of plasmid pSGS21 at 37° C. was determined and compared to the stability of plasmid pSGS4 (Table 1) at 30° C. (FIG. 2). Plasmid pSGS21 is perfectly stable after 200 generations of growth at 37° C. Agarose-gel analysis of 10 single cell colonies after 200 generations of growth showed identical plasmid size compared to pSGS21. The specific activities of anthranilate synthetase and valyl-tRNA synthetase were determined after 160 and 200 generations of growth. No signs of decrease in specific activities could be observed compared to the control (GRB238 carrying pSGS21 grown for 10 generations) indicating the integrity of the plasmid (Table 2).

MATERIALS AND METHODS

Mating procedure.

Transfer of ColE1 hybrid plasmid from strain JA200 was performed by F'-mediated transfer. Donor strain JA200 (valS+) and recipient strain GRB238 (valS$^{ts}$) were grown in LB medium to $2 \times 10^8$ cells/ml, mixed at the ratio 1:2 and mated for 5 hrs.

Isolation of plasmid DNA.

Plasmid DNA was isolated from 250 ml over night cultures grown in medium LB (Ref. 1) supplemented with medium E (Ref. 10) and 0.2% glucose at 37° C. The cells were harvested and washed once in ice cold 0.9% aqueous NaCl by centrifugation. The washed cells were resuspended in 8 ml 10 mM EDTA, 2 mg/ml lysozyme, 50 mM glucose, 25 mM Tris-Hcl pH 8.0 and incubated on ice for 30 min. 16 ml 0.2M NaOH 1% SDS was added and the incubation was continued for 5 min. 12 ml 3M Na-acetate pH 4.8 was added and the incubation was continued for 60 min. The mixture was centrifuged for 20 min. and 35,000 g at 4° C.

The supernatant was carefully removed and mixed with 0.6 vol of freeze cold isopropanol and incubated at $-20°$ C. for 20 min. The mixture was centrifuged at 27000 g at 4° C. for 5 min. The mixture was poured off and the tube walls were whiped dry. The pellet was resuspended in 4.0 ml dist. H$_2$O. 4.25 CsCl and 250 μl EtBr (5 mg/ml) were added and centrifuged in a Beckman Vti 65 rotor at 52000 rpm 10 hrs. The plasmid band was removed, EtBr was extracted 5 times with 3 volumes CsCl saturated isopropanol. The DNA was dialyzed in 10 mM Tris HCl pH 8.0, 1 mM EDTA and precipitated with EtOH.

DNA manipulations.

Conditions for use of restriction endonucleases and T4 DNA ligase were those suggested by the manufacturer (New England Biolabs, Inc. USA; Boehringer Mannheim, Germany). After restriction endonuclease digestion the enzymes were inactivated by incubation for 10 min. at 65° C. Analysis of plasmids and DNA fragments was performed by electrophoresis in horizontal agarose slab gels with Na-acetate (20 mM-EDTA), Tris-HCl (33 mM) pH 7.8 buffer.

Transformation.

Transformation of cells followed the procedure of Cohen et al (Ref. 3).

Plasmid stability test.

Bacterial strains containing plasmids to be tested for maintenance stability were inoculated on double selective agar plates minimal medium supplemented with medium E, 0.2% glucose 25 μg/ml tryptophan 10 μg/ml uracil and 30 μg/ml ampicillin. Cells from the selective plates were resuspended in fresh Minimal medium E supplemented with 25 μg/ml tryptophan and 10 μg/ml uracil to a cell density of about 10$^9$ per ml. The cultures were diluted 10$^6$ times and incubated on a rotary shaker at 37° C. or 30° C. After 20 generations of growth the cultures were diluted and the procedure was continued for at least 100 generations of growth in the non-selective medium. At appropriate time points aliquots of the cultures were diluted and spread on LA-plates. After incubation over night at 30° C., 100 colonies from each time point were tested for the presence of plasmid markers by transfer to Casa resp. LA+ampicillin plates using tooth picks.

Valyl-tRNA synthetase activity.

This activity was measured according to Marchin et al (Ref. 7).

Anthranilate synthetase activity.

For the assay of anthranilate synthetase $1.5 \times 10^9$ cells were harvested and washed once with cold 0.9% NaCl. The cells were resuspended in 0.2 ml 0.1M Tris-0.1% Triton X-100 pH 7.8, frozen in 15 min. at $-20°$ C. and thawed at $20°$ C.–$37°$ C. The "lysates" were stored on ice and the anthranilate synthetase activity was measured within 2 hours. An appropriate amount of extract in a total volume of 50 μl was added to 0.5 ml reaction mix (0.05M Tris-pH 7.8, 2 mM Mg acetate, 5 mM L-glutamine, 0.001M DTT and 0.15 mg/ml Barium chorismate). The reaction mixture was incubated with shaking for 20 min. at $37°$ C. The reaction was stopped by chilling and the addition of 0.1 ml 1M ammonium acetate, pH 4.5. 1.5 ml ethylacetate was added and the tubes were vortexed briefly for thorough mixing. The phases were separated by low speed centrifugation for 2 min. 0.5 to 1 ml of the ethyl acetate layer was removed for anthranilate determination in an Aminco-Bowman spectrophotofluorimeter (excitation 310 nm, emission 400 nm). Unknown samples are related to standard. Standard: 1 mM anthranilic acid was diluted 1 to 20 times. 50 μl of the dilution were added to 0.5 ml reaction mix and treated as above.

One unit of anthranilate synthetase is defined as the amount of enzyme which converts 0.1 μmole of chorismate to anthranilate in 20' min. at $37°$ C.

The plasmid of the invention, designated pSGS21 has been deposited, using *E. coli*, strain GRB238 as a host organism, with Deutsche Sammlung für Mikroorganismen, Göttingen, West Germany under deposition number DSM2765.

REFERENCES:

1. Bertani, G.: Studies on lycogenesis, I. the mode of phage liberation by lysogenic in *Escherichia coli*. J. Bacteriol. 62, (1951) 293–300.
2. Bolivar, F., Rodriguez, R. L., Greene, P. J., Betlach, M. C., Heyneker, H. L., Boyer, H. W., Crosa, J. H., and Falkow, S.: Construction and characterization of new cloning vehicles. II. A multipurpose cloning system. Gene 2, (1977) 95–113.
3. Cohen, S. N., Chang, A. C. Y., and Hsu, L.: Nonchromosomal antibiotic resistance in bacteria: Genetic transformation of *Escherichia coli* by R-factor DNA. Proc. Natl. Acad. Sci. USA 69. (1972) 2110–2114.
4. Clarke, L., and Carbon, J. A.: A colony bank containing synthetic ColE1 hybrid plasmids representative of the entire *Escherichia coli* genome. Cell 9, (1976) 91–99.
5. Enger-Valk, B. E., Heyneker, H. L., Oosterbaan, R. A., and Pouwels, P. H.: Construction of new cloning vehicles with genes of the tryptophan operon of *Escherichia coli* as genetic markers. Gene 9, (1980) 69–85.
6. Low, B.: Formation of merediploids in mating with a class of Rec⁻ recipient strains of *Escherichia coli* K-12. Proc. Natl. Acad. Sci. USA 60, (1968) 160–167.
7. Marchin, G. L., Comer, M. M., and Neidhardt, F. C.: Viral modification of the valyl transfer ribonucleic acid synthetase of *Escherichia coli* J. Bact. Chem. 247, (1972) 5132–5145.
8. Eidlic, L., and Neidhardt, F. C.: Protein and nucleic acid synthesis in two mutants of *Escherichia coli* with temperature-sensitive aminoacyl ribonucleic acid synthetases, J. Bacteriol, 89, (1965) 706–711.
9. Tingle, M. A., and Neidhardt, F. C.: Mapping of a Structural Gene for Valyl-Transfer Ribonucleic Acid Synthetase in *Escherichia coli* by Transduction. J. Bact. 98, (1969) 837–839.
10. Vogel, H. J., and Bonner, D. M.: Acetylornithinase of *Escherichia coli*: Partial purification and some properties. J. Biol. Chem. 218, (1956) 97–106.

TABLE 1

Strains of *E.coli* K12 used.

| Strain | Genotype or phenotype | Source/Comments |
|---|---|---|
| JA200 | trpE5, trh, leu, lacY, recA | Clarke and Carbon 1976 (ref. 4) |
| GRB238 | trp, ura, valS$^{ts}$, RecA, strR | NP910212Str mutant crossed with KL16-99 to get recA |
| NP910212 | trp, ura, valS$^{ts}$ | Tingle and Neidhart 1969 (ref. 9) |
| KL16-99 | recA | B. Low 1968 (ref. 6) |
| W 3110 | | C.G.S.C. (B. Backmann) |

| Plasmid | Genotype | Source/Comments |
|---|---|---|
| pBR322 | Ap$^r$ Tc$^r$ | Bolivar et al 1977 (ref. 2) |
| ColE1-valS | valS+ | Acc. to invention |
| pHOV1 | valS+Ap$^r$ | " |
| pSGS21 | valS+, trp+, Ap$^r$ | " |
| pHP39 | trp+ | Enger-Walk et al, 1980 (ref.5 ) |
| pSGS4 | trp+, Ap$^r$, Tc$^r$ | EcoR1-fragment carrying the trp-operon form pHP39 inserted in the EcoR1 site in pBR322. |

TABLE 2

| Strain | Plasmid | Rel valyl-tRNA synthetase activity | Rel anthranilate synthetase activity |
|---|---|---|---|
| W3110 | — | 1 | 1 |
| GRB238 | — | 0 | — |
| GRB238 | ColE1-valS+ | 2.6 | — |
| GRB238 | pHOV1 | — | — |
| GRB238 | pSGS21 | 6.2 | — |
| GRB238 | pSGS21 o/n* (10 g) | 7.8 | 5.1 |
| GRB238 | pSGS21 180 g | 7.3 | 7.6 |

*grown over-night

We claim:

1. A recombinant plasmid of stabilized inheritance, which comprises: a first nucleic acid fragment containing a production gene, said gene not normally found in the plasmid and encoding a polypeptide, and a second nucleic acid fragment containing a gene encoding valyltRNA synthetase, said first and second fragments each being situated in said plasmid so that each is operational, wherein said plasmid is one which is derived from an *E. coli* microorganism and wherein the plasmid containing said first and second nucleic acid fragments exhibits stabilized inheritance upon transformation and growth in a host *E. coli* microorganism due to expression of both the production gene and the valyl-tRNA synthetase gene.

2. A plasmid according to claim 1, wherein the production gene is directed to the production of a primary metabolite.

3. A plasmid according to claim 2, wherein the production gene is directed to the production of an amino acid.

4. A plasmid according to claim 3, wherein said amino acid is tryptophan.

5. An *E. coli* cell containing a plasmid according to claim 1, which cell lacks valyl-tRNA synthetase activity and which is constituted by a host strain carrying a mutation making the chromosomally mediated valyl-tRNA synthetase enzyme temperature sensitive.

6. A cell according to claim 5, the strain being GRB238.

* * * * *